(12) United States Patent
Guala

(10) Patent No.: US 11,000,639 B2
(45) Date of Patent: May 11, 2021

(54) PRESSURE POD FOR HAEMODIALYSIS MEDICAL LINES

(71) Applicant: Industrie Borla S.p.A., Moncalieri (IT)

(72) Inventor: Gianni Guala, Turin (IT)

(73) Assignee: INDUSTRIE BORLA S.P.A., Moncalieri (IT)

( * ) Notice: Subject to any disclaimer, the term of this patent is extended or adjusted under 35 U.S.C. 154(b) by 226 days.

(21) Appl. No.: 16/091,002

(22) PCT Filed: Apr. 5, 2017

(86) PCT No.: PCT/IB2017/051951
§ 371 (c)(1),
(2) Date: Oct. 3, 2018

(87) PCT Pub. No.: WO2017/175149
PCT Pub. Date: Oct. 12, 2017

(65) Prior Publication Data
US 2019/0060551 A1 Feb. 28, 2019

(30) Foreign Application Priority Data

Apr. 6, 2016 (IT) .......................... 102016000035281

(51) Int. Cl.
*A61M 1/36* (2006.01)
*A61M 39/10* (2006.01)
*A61M 1/16* (2006.01)

(52) U.S. Cl.
CPC .......... *A61M 1/3641* (2014.02); *A61M 39/10* (2013.01); *A61M 1/16* (2013.01)

(58) Field of Classification Search
CPC ...... A61M 1/3641; A61M 1/16; A61M 39/10; A61M 39/1011; A61M 39/105; A61M 39/12; A61M 39/14; A61M 39/18; A61M 2039/1005; A61M 2039/1016
See application file for complete search history.

(56) References Cited

U.S. PATENT DOCUMENTS

| 6,152,913 A | * | 11/2000 | Feith ..................... A61M 39/10 604/533 |
| 6,394,983 B1 | | 5/2002 | Mayoral et al. |
| 2007/0179422 A1 | * | 8/2007 | Schnell ............... A61M 1/3641 604/4.01 |

FOREIGN PATENT DOCUMENTS

| EP | 0736306 A1 | 10/1996 |
| EP | 1236481 A1 | 9/2002 |
| WO | 2015099932 A1 | 7/2015 |

OTHER PUBLICATIONS

International Search Report and Written Opinion of the International Searching Authority for PCT/IB2017/051951 dated Jun. 14, 2017.

* cited by examiner

*Primary Examiner* — Philip R Wiest
(74) *Attorney, Agent, or Firm* — Heslin Rothenberg Farley & Mesiti P.C.; Victor A. Cardona, Esq.

(57) ABSTRACT

A pressure pod for haemodialysis medical lines includes a hollow body with an intermediate flexible membrane which delimits a gas chamber and a liquid chamber with inlet and outlet tubular fittings for connection to the haemodialysis medical line. A female luer-lock connector has an outer tubular body and an inner tubular body on which the outer tubular body is axially blocked rotatably. A tubular fitting is engaged within an annular cavity formed between the inner and outer tubular bodies of the female connector.

7 Claims, 4 Drawing Sheets

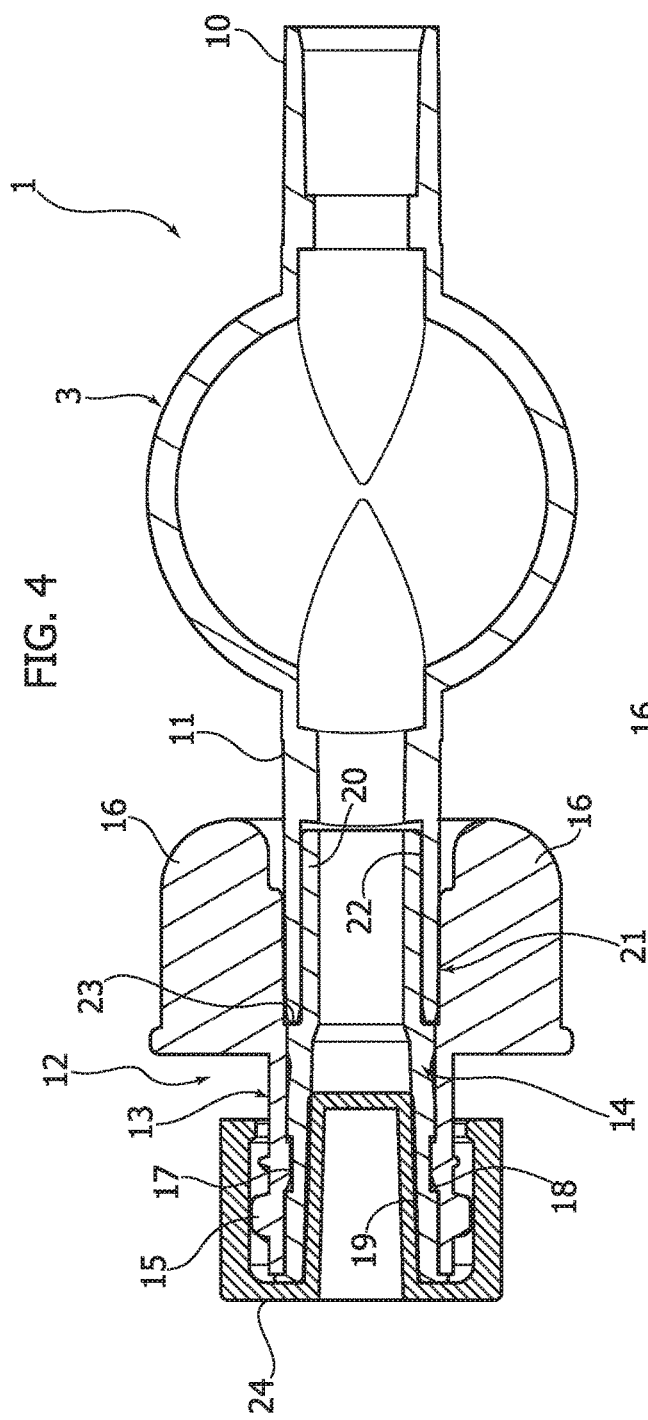
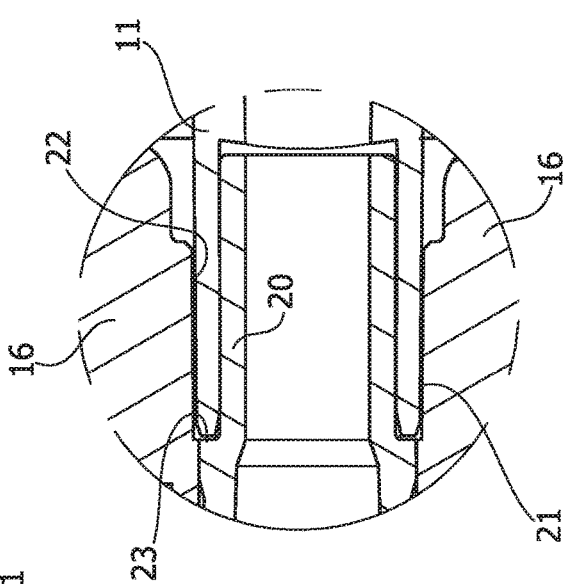

US 11,000,639 B2

PRESSURE POD FOR HAEMODIALYSIS MEDICAL LINES

CROSS REFERENCE TO RELATED APPLICATIONS

This application is a 371 national stage of PCT International Application No. PCT/IB2017/051951 filed on Apr. 5, 2017, and published in English on Oct. 12, 2017 as WO 2017/175149 A1, which claims priority to Italian Patent Application No. 102016000035281 filed on Apr. 6, 2016, the entire disclosures of which are incorporated herein by reference.

FIELD OF THE INVENTION

The present invention regards pressure pods for haemodialysis medical lines, of the type comprising a hollow body made up of an upper half-shell and a lower half-shell respectively delimiting a gas chamber and a liquid chamber hermetically separated from each other by an intermediate flexible membrane. The liquid chamber has inlet and outlet tubular fittings for connection to the haemodialysis line, and at least one of such tubular fittings, typically the outlet fitting intended to be connected to the dialysis machine, is associated to a female luer-lock connector for connecting the sensor to a duct.

STATE OF THE PRIOR ART

Pressure sensors of the type defined above, conventionally referred to as "pressure pods", are for example known from documents US-2007179422 and WO-2015099932 and they reveal a technical problem related to connection to the medical line. In particular, whereas on the one hand it is crucial that the outlet fitting of the liquid chamber be connected to the relative duct in an airtight fashion, it would be preferable that such connection also be rotatable, so as to enable relative angular movements between the pod and the duct that is normally flexible, with the aim of averting the risk of twisting and consequently obstructing the blood flow.

Document U.S. Pat. No. 6,152,913 describes a male luer lock connector whose internally threaded outer element rotates on the inner element, which is made of rigid plastic material. Documents EP-0736306 and EP-1236481, both on behalf of the Applicant, also describe male luer lock connectors with a rotatable outer element and an inner element made of rigid material.

SUMMARY OF THE INVENTION

The object of the present invention is to provide a safe and functional solution to the aforementioned technical problem, and this object is attained due to the fact that the female connector of the aforementioned at least one tubular fitting of the liquid chamber of the pressure pod comprises an outer tubular body made of relatively rigid thermoplastic material and an inner tubular body made of relatively soft thermoplastic material coaxially inserted into the outer tubular body. The outer tubular body is rotatable with respect to the inner tubular body and it is axially locked thereon, and an annular cavity in which the aforementioned at least one tubular fitting—which is fixed to the relatively soft inner tubular body—is engaged, is defined between respective proximal axial portions of the inner and outer tubular bodies.

Thanks to this solution idea, the connection of the pressure pod to the haemodialysis line can be advantageously obtained both in a perfectly airtight manner, due to the fixing of the tubular fitting on the inner tubular body made of relatively soft material, and rotatable, through the outer tubular body of the female connector, but simultaneously rigid to flexion.

Conveniently, the aforementioned annular cavity is radially delimited by a collar or outer annular stop of the proximal axial portion of the inner tubular body, against which it frontally abuts said at least one tubular fitting.

This characteristic enables facilitating the mechanised assembly between the female connector and the tubular fitting, further contributing to the perfect mutual airtight sealing.

According to a further characteristic of the invention, the pod further comprises a male luer protection cap applied to said female connector in a hermetic and removable fashion.

BRIEF DESCRIPTION OF THE DRAWINGS

The invention will now be described in detail, purely by way of non-limiting example, with reference to the attached drawings, wherein:

FIG. 4 is a longitudinal sectional view according to line IV-IV of FIG. 3, and FIG. 5 shows—in larger scale—a detail of FIG. 4.

DETAILED DESCRIPTION OF THE INVENTION

Figure 1:
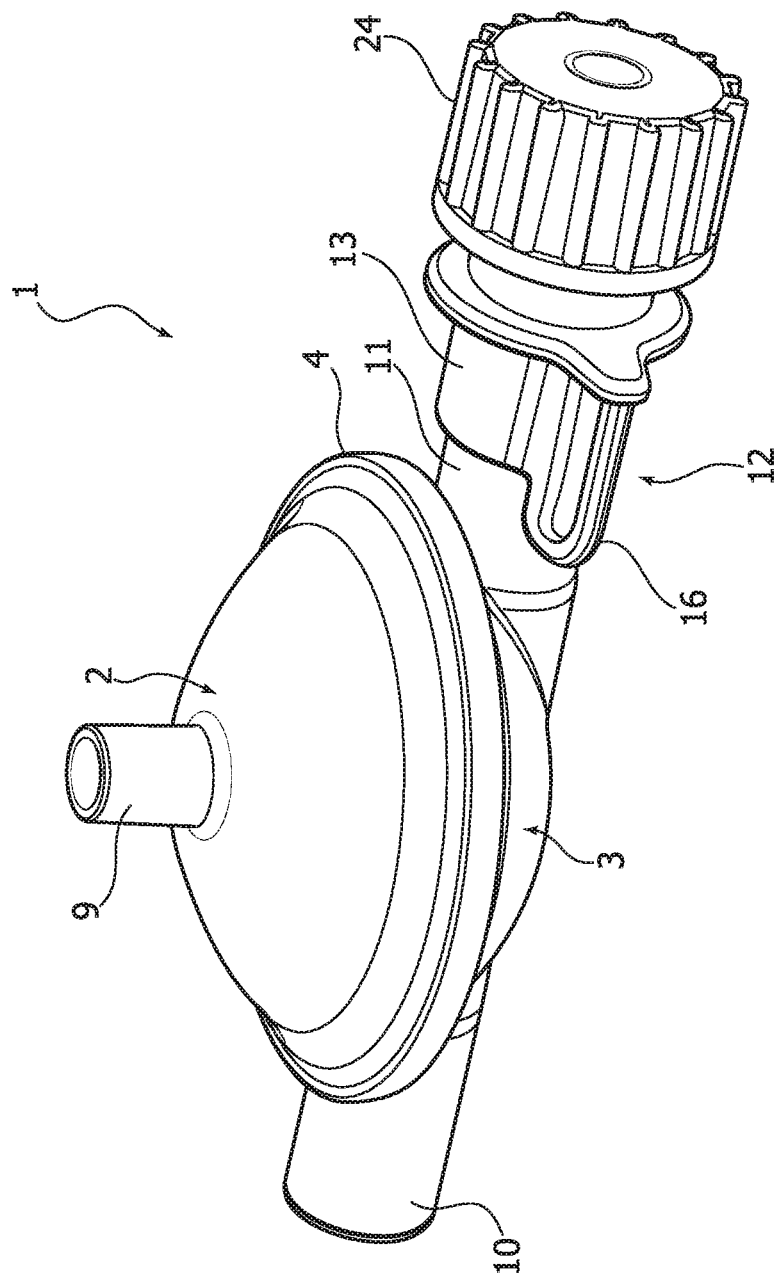
FIG. 1 is a schematic perspective view of a pressure pod for haemodialysis medical lines according to the invention.
Figure 2:
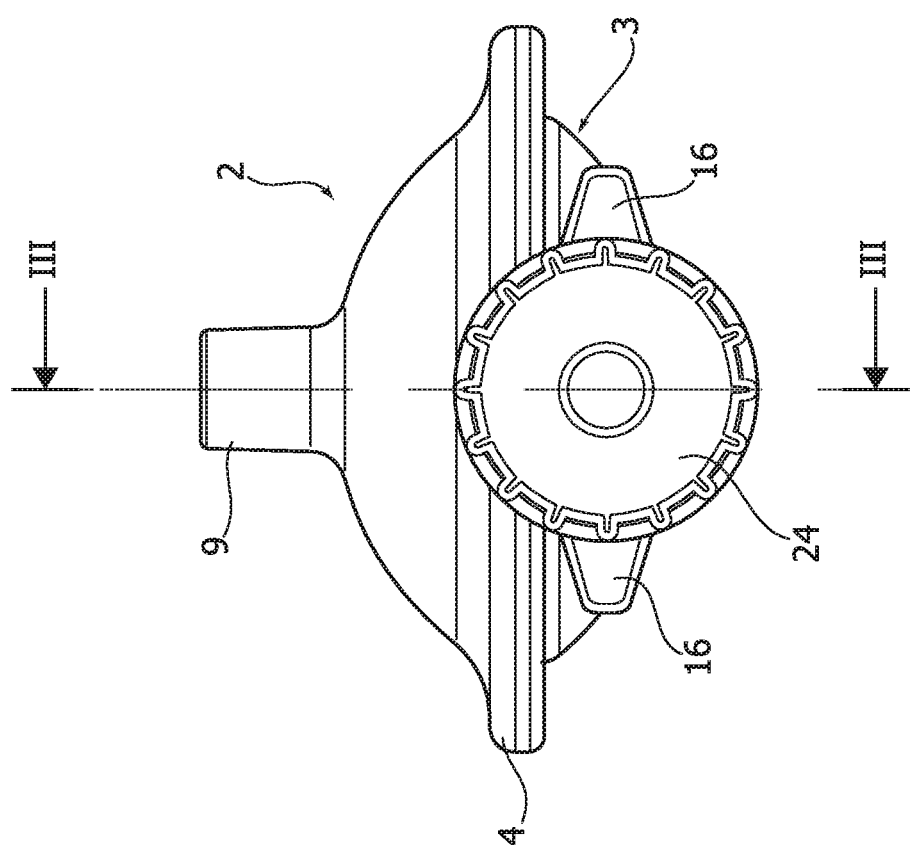
FIG. 2 is a front elevational view—and in larger scale—of the pressure pod.
Figure 3:
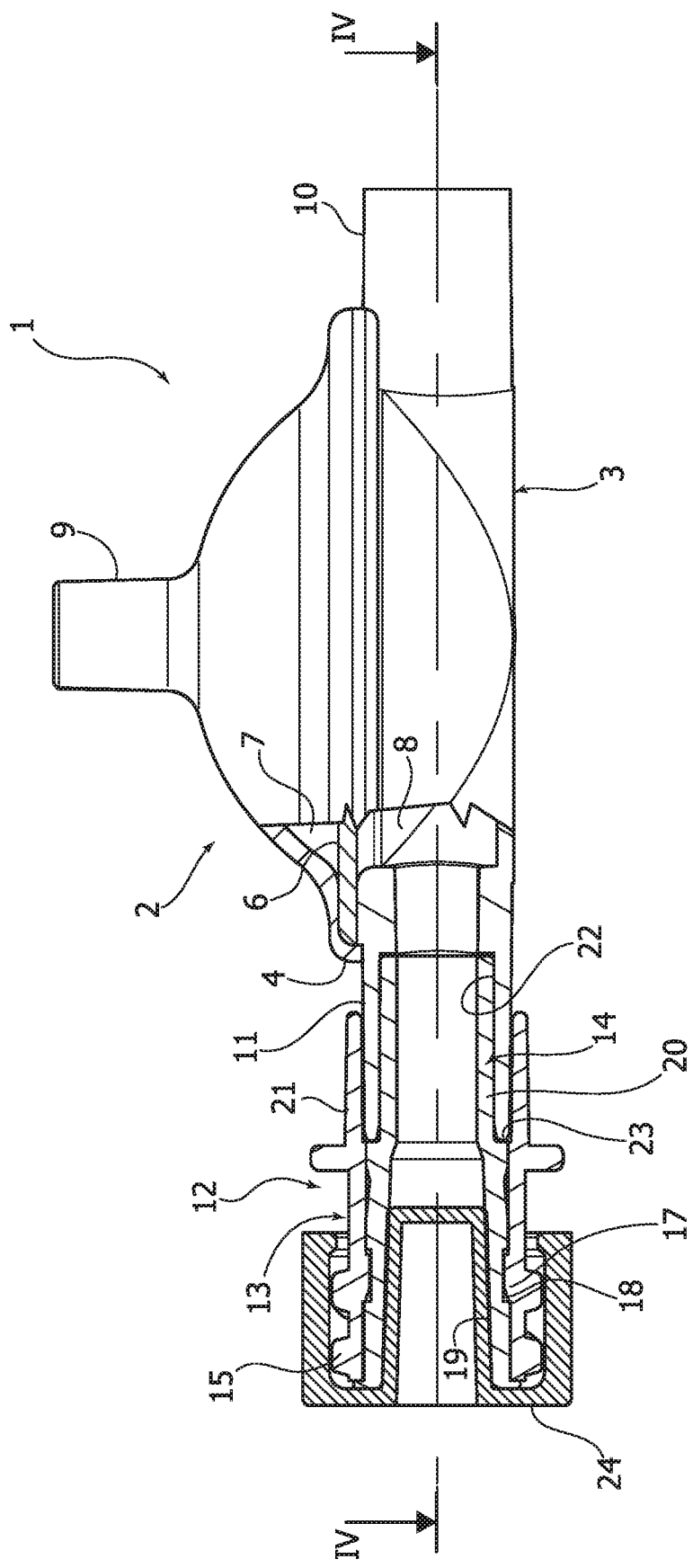
FIG. 3 is a partial longitudinal sectional view according to line III-III of FIG. 2.

With reference to the drawings, a pressure pod for haemodialysis medical lines according to the invention is indicated in its entirety with 1.

The pressure pod 1 consists in a hollow body made of moulded plastic material formed by an upper half-shell 2 and by a lower half-shell 3 whose perimeter edges are hermetically connected to each other in 4 by interposing an intermediate flexible membrane 6.

The membrane 6 delimits a gas chamber 7 and a liquid chamber 8, mutually hermetically separated respectively with the upper half-shell 2 and the lower half-shell 3.

The upper half-shell 2 is integrally formed with a tubular fitting 9 for connecting the gas chamber 7 to a pressure measuring device of the known type, in turn connected to an electronic unit that regulates the amount of gas in the chamber 7 so as to control the position of the membrane 6.

The lower half-shell 3 is integrally formed, on opposite sides, with an inlet tubular fitting 10 and an outlet tubular fitting 11 for connecting the pressure pod 1 to a haemodialysis medical line.

At least one of the fittings 10, 11, and in the case of the illustrated example the outlet fitting 11, is provided with a female luer-lock connector 12 for attaching a supplementary male luer lock connector of a duct of the medical line, usually connected to the dialyser.

According to the distinctive characteristic of the invention, the female connector 12 is formed by an outer tubular body 13 made of relatively rigid thermoplastic material, and an inner tubular body 14 made of relatively soft thermoplastic material, coaxially inserted in the outer tubular body 13. The general configuration of the female connector 12 may be similar to the one described and illustrated in EP-0775501B1, on behalf of the Applicant, but with the substantial difference to be outlined hereinafter.

The outer tubular body 13 is formed—on one side—with an outer threading 15 for fastening the male luer lock connector, and—on the opposite side—with a pair of juxtaposed manoeuvre radial fins 16, through which the rotation of the outer tubular body 13 is comfortably controlled. Internally, the outer tubular body 13 is formed with an annular relief 17 for the rotatable axial retention thereof in a corresponding outer annular groove 18 of the inner tubular body 14.

The inner tubular body 14 defines—at the distal end thereof—a luer cone 19, and the proximal axial portion thereof—indicated with 20—forms—with the proximal axial portion 21 of the outer tubular body 13—an annular cavity 22 inside which the tubular fitting 11 of the lower half-shell 3 is engaged. Such tubular fitting 11 is hermetically sealingly fixed, by gluing for example, on the proximal portion 20 of the inner tubular body 14, while the proximal portion 21 of the outer tubular body 13 is rotatable on such tubular fitting 11.

This arrangement is used to obtain—between the pressure pod 1 and the duct of the haemodialysis line—a connection that is rotatable but simultaneously rigid to flexion, with the guarantee of a perfect hermetic sealing and without risk of inadvertent blocking of the duct.

As illustrated in detail in FIG. 5, the annular cavity 22 is radially delimited by a collar or outer annular stop 23 of the proximal portion 20 of the inner tubular body 14, against which the end of the tubular fitting 11 frontally abuts so as to further increase efficiency in terms of perfect hermetic sealing connection thereof with the female connector 12.

A male luer protection cap removably applied to the female connector 12, is indicated with 24. The protection cap 24 is obviously removed when the pressure pod 1 is connected to the haemodialysis medical line.

Obviously, the construction details and the embodiments may widely vary with respect to what has been described and illustrated, without departing from the scope of protection of the invention, as defined in the claims that follow.

The invention claimed is:

1. A pressure pod for haemodialysis medical lines comprising:

a hollow body formed by an upper half-shell and a lower half-shell which delimit a gas chamber and a liquid chamber, respectively, hermetically separated from each other by an intermediate flexible membrane, the liquid chamber having inlet and outlet tubular connectors for connection to a haemodialysis line, and a female connector comprising an outer tubular body made of a relatively rigid thermoplastic material and an inner tubular body made of a relatively soft thermoplastic material coaxially fitted within the outer tubular body, said outer tubular body being rotatable relative to the inner tubular body and axially blocked thereon to inhibit movement of said outer tubular body distally and proximally relative to said inner tubular body, an annular cavity defined between proximal axial portions of the inner and outer tubular bodies, and at least one of said tubular connectors received within said annular cavity and connected to said inner tubular body of the female connector.

2. The pressure pod according to claim 1, wherein said annular cavity is radially delimited by an outer annular stop of said proximal axial portion of the inner tubular body against which said at least one tubular fitting is frontally abutting.

3. The pressure pod according to claim 1 further comprising a male luer protection cap releasably applied to said female connector.

4. The pressure pod according to claim 1, wherein said proximal axial portion of the outer tubular body comprises radially projecting manoeuvre fins.

5. The pressure pod according to claim 2 further comprising a male luer protection cap releasably applied to said female connector.

6. The pressure pod according to claim 2, wherein said proximal axial portion of the outer tubular body comprises radially projecting manoeuvre fins.

7. The pressure pod according to claim 3, wherein said proximal axial portion of the outer tubular body comprises radially projecting manoeuvre fins.

* * * * *